United States Patent [19]

Fisher et al.

[11] 4,320,129

[45] Mar. 16, 1982

[54] PYROMELLITIC DIIMIDE COMPLEXES

[75] Inventors: Michael H. Fisher; Bruce O. Linn, both of Bridgewater, N.J.

[73] Assignee: Merck & Co., Inc., Rahway, N.J.

[21] Appl. No.: 9,204

[22] Filed: Feb. 5, 1979

[51] Int. Cl.[3] ........................................... C07D 239/20
[52] U.S. Cl. .................................. 424/251; 424/263; 424/274; 546/290; 544/315; 260/326 R
[58] Field of Search ....................... 424/274, 251, 263; 544/315; 546/290; 260/326 R

[56] References Cited

U.S. PATENT DOCUMENTS

| | | | |
|---|---|---|---|
| 2,731,382 | 1/1956 | Basso et al. | 167/63.1 |
| 2,731,383 | 1/1956 | O'Neill et al. | 167/53.1 |
| 2,731,384 | 1/1956 | O'Neill et al. | 167/53.1 |
| 3,329,668 | 2/1967 | McKay et al. | 260/96.5 R |
| 3,926,935 | 12/1975 | Rogers et al. | 260/96.5 C |

OTHER PUBLICATIONS

CA vol. 83 78285e (1975).
CA vol. 74 126131q (1971).
CA vol. 75 21210g (1971).
CA vol. 73 98559n (1970).
CA vol. 72 3176j (1970).
CA vol. 67 117731p (1967).

*Primary Examiner*—Nicholas S. Rizzo
*Attorney, Agent, or Firm*—David L. Rose; Harry E. Westlake

[57] ABSTRACT

Complexes of pyromellitic diimide compounds which are ruminant feed additives and which improve feed efficiency are disclosed. The pyromellitic diimide compounds may be unsubstituted pyromellitic diimide itself, or one of the nitrogen atoms may be substituted with an alkyl or substituted alkyl group. The pyromellitic diimide nucleus may also be substituted. The pyromellitic diimide compound is complexed with a compound containing an amide, amidine or thioamide linkage. The complexing agent may be either cyclic or open chain. Compositions using the complexes as ruminant feed additives are also disclosed.

11 Claims, No Drawings

PYROMELLITIC DIIMIDE COMPLEXES

SUMMARY OF THE INVENTION

The novel complexes of this invention are prepared from N-unsubstituted or N-mono-substituted pyromellitic diimides and an amide, thioamide, or amidino compound. The complexing agent may be either a cyclic or open chain compound. Such complexes are useful as feed additives for ruminants. Thus it is an object of this invention to describe such complexes. A further object of this invention is to describe processes for the preparation of such complexes. A still further object is to describe the use of such compounds for the administration to ruminant animals in order to increase feed efficiency, to shift the production of volatile fatty acids away from acetate with an increase in propionate and butyrate and to suppress methane formation. Further objects will become apparent from a reading of the following description.

DESCRIPTION OF THE INVENTION

The pyromellitic diimide complexes of this invention are best described in the following structural formula:

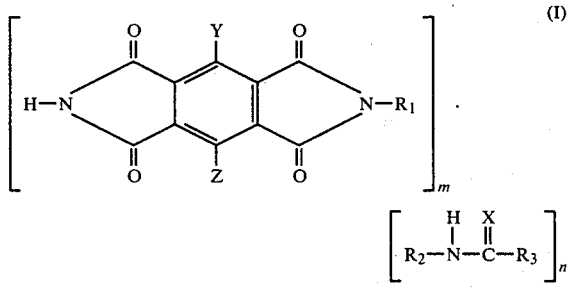

wherein
- m and n are independently 1 or 2 such that m and n are not both 2;
- $R_1$ is hydrogen, loweralkyl, or hydroxy substituted loweralkyl;
- Y and Z are independently hydrogen, halogen or loweralkyl;
- X is oxygen, sulfur or imino;
- $R_2$ and $R_3$ are independently hydrogen, loweralkyl, amino, aminoloweralkyl, loweralkylamino; and
- $R_2$ and $R_3$ may be connected to form a 5- or 6-membered heterocyclic ring containing one, two or three nitrogen atoms which may be optionally substituted with loweralkyl, or hydroxy.

In the instant application, the term "loweralkyl" is intended to include those alkyl groups of from 1 to 6 carbon atoms in either a straight or branched configuration. Exemplary of such groups are methyl, ethyl, propyl, isopropyl, butyl, sec-butyl, tert-butyl, pentyl, isopentyl, hexyl, and the like.

The preferred complexes of this invention are realized in the above structural formula when $R_1$ is hydrogen, methyl, ethyl, or hydroxyethyl; and Y and Z are hydrogen. The most preferred pyromellitic diimide compounds are those when Y and Z are hydrogen and $R_1$ is hydrogen, methyl or hydroxy ethyl.

The preferred complexing agents are described when $R_2$ is hydrogen or loweralkyl; $R_3$ is hydrogen, amino or loweralkyl; and X is oxygen. Further preferred compounds are realized when $R_2$ and $R_3$ are connected to form a pyridyl or a pyrimidinyl ring, optionally substituted with loweralkyl or hydroxy; and X is oxygen or imino. The more preferred complexing agents are urea, formamide, acetamide, 2-pyridone or 2- or 4-pyrimidone optionally substituted with methyl, or hydroxy; and 2 or 4 amino pyrimidine optionally substituted with methyl.

The most preferred complexing agents are urea, formamide, acetamide, 4,6-dimethyl-2-pyrimidone, 2,4-dimethyl-6-pyrimidone, 2-pyridone, 3-hydroxy-2-pyridone and 2-amino-4,6-dimethyl pyrimidine.

It will be appreciated by those skilled in this art that the cyclic amides, thioamides and amidines of this invention exist as tautomeric mixtures. That is for example, 2-pyridone may also be described as 2-hydroxy pyridine; 2-pyrimidone may also be described as 2-hydroxy pyrimidine; and 2-amino pyrimidine may also be described as 2-imino pyrimidine. The tautomeric forms of the above groups are represented in the following equilibrium formulae:

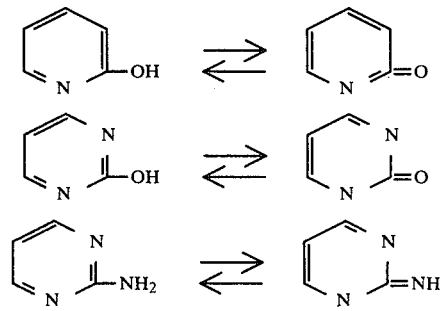

for convenience, the cyclic amides, thioamides and amidines of this invention will be represented in the oxo, thio and imino forms.

Pyromellitic diimide ($R_1$=H) has two reactive sites and N-monosubstituted pyromellitic diimide ($R_1\neq$H) has one reactive site available for complexing. Thus when $R_1$=H, it is possible to form complexes in the ratio of 1:1 (m=n=1) 1:2 (m=1,m=2) and 2:1 (m=2,n=1). When $R_1$ is other than hydrogen, complexes may be formed in the ratio of 1:1 (m=n=1) and 1:2 (m=1,n=2). Complexes with other than equimolar quantities of the pyromellitic diimide compound are generally formed by using the appropriate ratio of starting materials. However, whether equimolar quantities of starting materials are used or not, solvent effects can have a profound effect on the nature of the complex isolated. When more than one complex ratio is capable of being formed, and one particular ratio is highly insoluble in the particular solvent system being employed, then that ratio will be the one predominantly isolated. By changing the solvent system to one in which the undesired complex is more soluble, and the preferred complex less soluble, the desired complex ratio may be achieved. In addition, in certain cases an excess of complexing agent may be used, such as where the complexing agent is a liquid, the solvent can be reduced or eliminated. Also, occasionally an increase in yield is noted when the complexing agent is used in excess.

The pyromellitic diimide complexes with the instant complexing agents are new chemical compounds. They are discrete stoichiometric entities which have their own characteristic properties that are markedly different from the component parts and are not mere mixtures of the pyromellitic diimide and the complexing agent.

The complexes of the instant invention are prepared by combining the pyromellitic diimide compound with the complexing agent in an aprotic solvent in which both reagents are soluble and which will be non-reactive with the reagents. The preferred solvents are dimethylformamide, ether, acetone, dimethylacetamide, dimethylsulfoxide, 1-methyl-2-pyrrolidinone and the like. Very often mixtures of solvents are employed in order to obtain particular solubility characteristics. After combining in the solvent, the mixture is stirred for from 1 hour to 4 days, at from about room temperature to the boiling point of the reaction mixture. It is preferred to carry out the reaction at room temperature. The complexes are isolated using techniques known to those skilled in this art.

The complexing agents of this invention are known compounds as is pyromellitic diimide ($R_1$=H). The compounds with other values of $R_1$ are prepared according to the following reaction scheme:

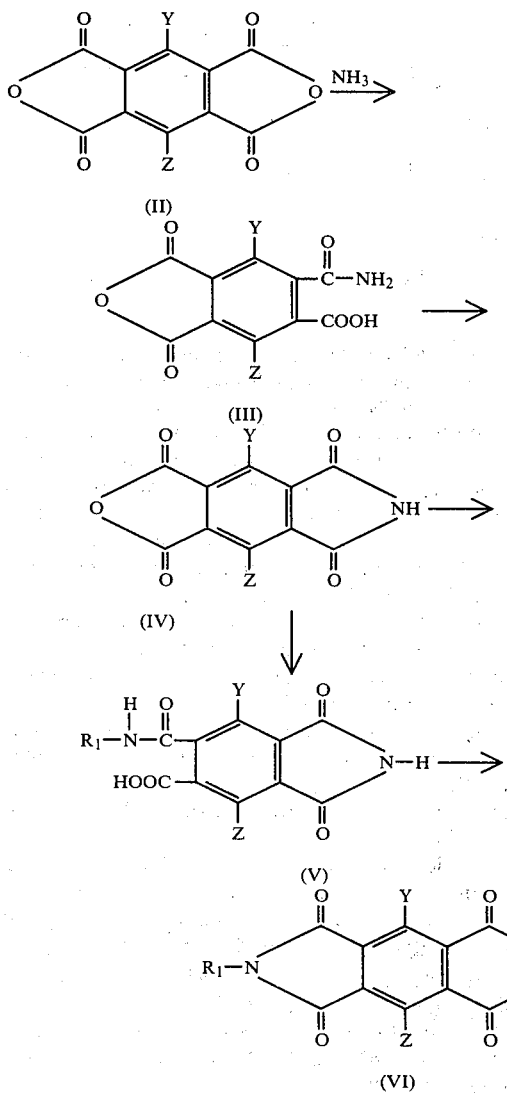

In the foregoing reaction scheme pyromellitic dianhydride (II) is treated with ammonia to prepare the 1-carbamoyl-2-carboxybenzene-4,5-dicarboxylic anhydride (III). The reaction is generally carried out in a non-polar solvent in which the starting material is soluble such as tetrahydrofuran, acetone, and the like and is complete in from 5 minutes to 2 hours at from 0° C. to room temperature. Room temperature is preferred.

Compound III is then heated with thionyl chloride at about room temperature to the reflux temperature of the reaction mixture for from ½ to 16 hours to prepare the pyromellitic imide anhydride (IV). Generally the reaction is carried out without any solvent using an excess of thionyl chloride, however, if desired, a non-polar solvent, such a benzene or toluene may be employed. Alternatively the cyclization may be carried out by heating in a high boiling solvent such as dimethylformamide, dimethylsulfoxide, dimethylacetamide, diphenyl ether and the like at from about 100° C. to the reflux temperature of the reaction mixture. The reaction is complete in about ½ to 1 hour to prepare compound (IV).

Compound (IV) is then treated with an $R_1$ substituted amine to react with the anhydride portion of compound (IV) and prepare the $R_1$ carbamoyl compound (V). The reaction is generally carried out in a solvent as described above and is complete in about 5 minutes to 2 hours at from about 10° to 50° C. Room temperature is preferred.

The carbamoyl compound (V) is heated in a high boiling solvent as described above to prepare the $R_1$ monosubstituted pyromellitic diimide (VI). The products are isolated using techniques known to those skilled in this art.

Alternatively the pyromellitic imide anhydride (IV) may be reacted without isolating the intermediate (V). The initial reaction with one mole of the amine may be carried out in a high boiling solvent such as dimethylformamide, but at the temperature conditions above described for the amine step. Then, after the prescribed reaction times the reaction mixture may be slowly brought (over a period of from 1 to 4 hours) to the reaction conditions of the second step. The product (VI) will be isolated in the usual manner.

In a further variation of the foregoing process, the order of the ammonia and amine reactions may be reversed. That is, in the processes II→III the ammonia may be replaced with the $R_1$-$NH_2$ of step IV→V. In this way the $R_1$ group is placed on the intermediates at the outset. The ammonia is then used in step IV→V. There is no difference in the product between the two process variations, and either process may be employed to prepare the pyromellitic diimide compounds of this invention.

In the course of investigating the efficiency of feed use, the mechanism by which ruminants digest and degrade the components of their feed to form molecules which can be metabolically utilized has been intensively studied. The mechanism of carbohydrate utilization is now well known. Microorganisms in the rumen of the animal ferment the carbohydrate to produce monosaccharides and then degrade the monosaccharides to pyruvate compounds.

Pyruvate is then metabolized by microbiological processes to either acetate or propionate compounds, which may be either acids or other forms of the radicals. Two acetate radicals may be combined thereafter, still in the rumen, to form butyrates.

The animal can utilize butyrate, propionate, and acetate with differing degrees of efficiency. Utilization of these compounds which are collectively known as volatile fatty acid (VFA) occurs after absorption from the gut of the animal. Butyrate is utilized most efficiently, and acetate the least efficiently. However, the relative efficiency of use to butyrate is negated by the inefficiency of the manufacture of butyrate, which must be made from acetate in the rumen.

One of the major inefficiencies in the rumen is in the manufacture of acetate. Since it is made by the degradation of a pyruvate molecule, each molecule of acetate which is produced is accompanied by a molecule of methane. Most of the methane produced is lost through eructation. Since butyrate is made from two molecules of acetate, each molecule of the relatively efficiently used butyrate involves the loss to the animal of two molecules of methane, with all of the associated energy.

Thus, the efficiency of carbohydrate utilization (carbohydrates being the major nutritive portion of ruminant animals' feed) can be increased by treatments which encourage the animal to produce propionate rather than acetate from the carbohydrates. Further, the efficiency of feed use can be effectively monitored by observing the production and concentration of propionate compounds in the rumen. If the animal is making more propionates, it will be found to be using its feed more efficiently. This efficiency is manifested by greater weight gains per feed intake, a reduction in energy losses by methane release, and economic advantages to the animal grower when the animal is sold for consumption.

The method of improving the feed utilization of ruminants of this invention comprises orally administering to a ruminant an effective amount of one or more of the above-described novel complexes. Of course, the most economically important ruminant animals (those with multiple stomachs, one of which functions as a rumen) are cattle, sheep and goats. The complexes of this invention are administered to ruminants orally at rates of from about 0.1 mg./kg./day to about 10 mg./kg./day. While that range is functional, the preferred range of rates is from about 0.5 to 5 mg./kg./day.

It has been found that the complexes of this invention increase the efficiency of feed utilization in ruminant animals. The easiest way to administer the complexes is by mixing them in the animal's feed. However, the complexes of this invention can be usefully administered in other ways. For example, they can be incorporated into tablets, drenches, boluses, or capsules, and dosed to the animals. Formulation of the complexes in such dosage forms can be accomplished by means and methods well known in the veterinary pharmaceutical art. Each individual dosage unit should contain a quantity of the feed-efficiency-improving complex which has a direct relation to the proper daily dose for the animal to be treated.

Capsules are readily produced by filling gelatin capsules with any desired form of the desired complex. If desired, the complex can be diluted with an inert powdered diluent, such as a sugar, starch or purified crystalline cellulose, in order to increase its volume for convenience in filling capsules.

Tablets of the complexes useful in this novel method are made by conventional pharmaceutical processes. Manufacture of tablets is a well-known and highly-advanced art. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator as is alginic acid. Surface active agents such as sodium lauryl sulfate and dioctyl sodium sulphosuccinate are also sometimes used. Commonly used absorbents again include starch and lactose, while magnesium carbonate is also useful for oily substances. Frequently used binders are gelatin, gums, starch, dextrin and various cellulose derivatives. Among the commonly used lubricants are magnesium stearate, talc, paraffin wax, various metallic soaps, and polyethylene glycol.

This method of increasing the efficiency of feed utilization can also be practiced by the administration of the instant complexes as a slow-pay-out bolus. Such boluses are made as tablets are made, except that a means to delay the dissolution of the compound is provided. Boluses are made to release for lengthy periods. The slow dissolution is assisted by choosing a highly water-insoluble form of the complex. A substance such as iron fillings is added to raise the density of the bolus and keep it static on the bottom of the rumen.

Dissolution of the complex is delayed by use of a matrix of insoluble materials in which the drug is embedded. For example, substances such as vegetable waxes, purified mineral waxes, and water insoluble polymeric materials are useful.

Drenches containing a suspension of the complexes can be prepared in non-solvents such as vegetable oils such as peanut, corn, or sesame oil.

Suitable physiologically acceptable adjuvants are necessary in order to keep the complex suspended. The adjuvants can be chosen from among the thickeners, such as polyvinylpyrrolidone, gelatin, and the like. Many classes of surfactants also will serve to suspend the complexes. For example, lecithin, polyethylene oxide adducts, naphthalene sulfonates, alkylbenzenesulfonates and the polyoxyethylene sorbitan esters are useful for making suspension in liquid nonsolvents.

In addition, many substances which effect the hydrophilicity, density, and surface tension of the liquid can assist in making suspensions in individual cases. For example, silicone anti-foams, can be a useful suspending agent.

The suspendable complex may be offered to the animal grower as a suspension, or as a dry mixture of the compound and adjuvants to be diluted before use.

The most practical way to treat animals with the complexes of this invention usable in this novel method is by the formulation of the complex into the feed supply. Any type of feed may be medicated with the instant complexes, including common dry feeds, liquid feeds, and pelleted feeds.

The methods of formulating drugs into animal feeds are well known. It is usual to make a concentrated drug premix as a raw material for medicated feeds. For example, typical drug premixes may contain from about 1 to about 400 g. of drug per pound (454 g.) of premix. The wide range results from the wide range of concentration of drug which may be desired in the final feed. Premixes may be either liquid or solid.

The formulation of ruminant feeds containing the proper amounts of the instant complexes for useful treatment is mainly a matter of arithmetic. It is necessary only to calculate the amount of complex which it is desired to administer to each animal, to take into account the amount of feed per day which the animal eats, and the concentration of complex in the premix to be used, and calculate the proper concentration of the complex in the feed.

All of the methods of formulation, mixing, and pelleting feeds which are normally used in the ruminant feed art are entirely appropriate for manufacturing feeds containing the complexes usable in this method.

It is not intended that the scope of this invention be limited to any particular formulations or methods of administration. The invention is a method of increasing the efficiency of feed utilization by ruminant animals by the oral administration of certain complexes regardless of the method of administration of the compounds.

It is usual to treat economic animals, including ruminants, with a variety of growth promoters, disease preventives, and disease treatments throughout their lives. Such drugs are often used in combination. The novel method may be practiced in combination with other treatments.

EXAMPLE 1

Pyromellitic diimide.urea complex

To a solution of 12.0 gm. (0.20 mole) of urea in 900 ml. of dimethylformamide is added 21.6 gm. (0.10 mole) of pyromellitic diimide with stirring at room temperature (23° C.). The diimide gradually dissolves giving a clear solution. After 1 hour, 900 ml. of ethyl ether is added dropwise rapidly. A precipitate forms and the mixture is stirred at room temperature overnight (16 hours). The insolubles are collected, rinsed thoroughly with ethyl ether, and dried in vacuo at room temperature furnishing 20.1 gm. of product. The filtrate is further diluted with ethyl ether giving an additional 6.3 gm. of product and providing a total of 26.4 gm. of pyromellitic diimide.urea complex, m.p. >300° C.

EXAMPLE 2

Following the procedure of Example 1, the following complexes are obtained:

| Complex | m.p. °C. |
| --- | --- |
| N-methylpyromellitic diimide . urea | 239–240 |
| N-(2-hydroxyethyl)pyromellitic diimide . urea | 210–211 |

EXAMPLE 3

Pyromellitic diimide.formamide complex

To 21.6 gm. (0.10 mole) of powdered pyromellitic diimide in 860 ml. of dimethylformamide is added with stirring 20 ml. of formamide at room temperature. The mixture is stirred at room temperature (23° C.) for 16 hours. The insoluble pyromellitic diimide formamide complex is collected, rinsed thoroughly with cold acetone and dried in high vacuum at room temperature. There is obtained 9.7 gm. of pyromellitic diimide.formamide complex with a m.p. above 300° C. A precipitate separates from the dimethylformamide, acetone filtrate furnishing an additional 9.2 gm. of product.

EXAMPLE 4

Following the procedure of Example 3, the following complexes are obtained:

| Complex | m.p. °C. |
| --- | --- |
| Bis-[methylpyromellitic diimide] . formamide | >300 |
| Bis-[N-(2-hydroxyethyl) pyromellitic diimide] . formamide | 261–263 |
| Pyromellitic diimide . acetamide | >300 |
| Pyromellitic diimide . 4-amino-2,6-dimethylpyrimidine | >300 |

Following the above procedure, using equimolar quantities of 2-pyrrolidinone or 2-imidozolidone, in place of the formamide, there is obtained pyromellitic diimide.2-pyrrolidinone and pyromellitic diimide.2-imidazolidone respectively.

EXAMPLE 5

Pyromellitic diimide.4,6-dimethyl-2-pyrimidone complex

To a solution of 4,6-dimethyl-2-pyrimidone, 1.60 g. (10 moles), in 60 ml. of dimethylformamide is added 2.16 g. (10 mmoles) of pyromellitic diimide. The mixture is stirred at room temperature (23° C.) for 16 hours. The insolubles are filtered, rinsed with ethyl ether and dried in vacuo at room temperature furnishing 1.21 g. of pyromellitic diimide.4,6-dimethyl-2-pyrimidone complex, m.p. 275°–277° C. dec.

Following the above procedure, using equimolar quantities of 2-amino imidazole or 2-amino-4,5-dimethylimidazole in place of the 4,6-dimethyl-2-pyrimidone, there is obtained pyromellitic diimide.2-amino imidazole and pyromellitic diimide.2-amino-4,5-dimethylimidazole.

EXAMPLE 6

Pyromellitic diimide.bis-4,6-dimethyl-2-pyrimidone complex

To a solution containing 35.2 gm. (0.22 mole) of 4,6-dimethyl-2-pyrimidone dihydrate in 800 ml. of dimethylformamide is added 21.6 gm. (0.10 mole) of powdered pyromellitic diimide at room temperature (23° C.). The mixture is stirred at room temperature for 20 hours. The insolubles are collected, rinsed thoroughly with acetone and ether, and dried in vacuo at room temperature furnishing 19.1 gm. of pyromellitic diimide.bis[4,6-dimethyl-2-pyrimidone] complex, m.p. 284° C. dec. A second crop, 10.7 gm., is obtained from the filtrate.

EXAMPLE 7

Following the procedures of the foregoing Examples the following complexes are obtained:

| Complex | m.p. °C. |
| --- | --- |
| Pyromellitic diimide . bis[2,4-dimethyl-6-pyrimidone] | 242–244 |
| Pyromellitic diimide . bis[2-pyridone] | >300 |
| Pyromellitic diimide . bis[3-hydroxy-2-pyridone] | >300 |
| Pyromellitic diimide . bis[2-amino-4,6-dimethylpyrimidine] | >300 |

EXAMPLE 8

N-Methylpyromellitic diimide[4,6-dimethyl-2-pyrimidone] complex

A suspension of 1.60 g. (10 mmole) of 4,6-dimethyl-2-pyrimidone dihydrate, and 1.15 g. (5.0 mmole) of N-methylpyromellitic diimide, in 35 ml. of dimethylformamide is stirred with warming to 100° C. until solution occurs. The solution is cooled at room temperature until crystals form and then in an ice bath until crystallization is complete. The crystals are collected, rinsed thoroughly with ethyl ether and then dried in vacuo at room temperature furnishing 1.90 g. of N-methylpyromellitic diimide.[4,6-dimethyl-2-pyrimidone] complex m.p. 261°–263° C. characterized by i.r., n.m.r. and elemental analyses.

EXAMPLE 9

Applying the method of Example 8, the following complexes are prepared:

| Complex | m.p. °C. |
| --- | --- |
| N-Methylpyromellitic diimide . [2,4-dimethyl-6-pyrimidone | >300 |
| N-Methylpyromellitic diimide . [2-pyridone] | >300 |
| Pyromellitic diimide . [thiourea] | >300 |

PREPARATION 1

Pyromellitic imide anhydride

90 G. of 1-carbamoyl-2-carboxybenzene-4,5-dicarboxylic anhydride is added to 900 ml. of thionylchloride with stirring at room temperature. The reaction mixture is heated at reflux for 2 hours. Upon cooling, 900 ml. of hexane is added and the mixture stirred for 30 minutes. The insoluble material is filtered, washed with hexane and dried at 80° C. under vacuum affording 89.3 g. of a light yellow solid identified by infrared spectroscopy as pyromellitic imide anhydride.

PREPARATION 2

1 N-Ethylcarbamoyl 2-carboxybenzene 4,5-dicarboxylic acid imide 1.05 G. of pyromellitic imide anhydride is dissolved in 35 ml. of acetone and cooled to 0° C., 544 mg. of ethylamine dissolved in 10 ml. of acetone is added dropwise with stirring at 0° C. over a period of 15 minutes. The reaction mixture stirred at 0° C. for 20 minutes and concentrated to dryness in vacuo. The residue is dissolved in 9 ml. of water and centrifuged to remove the insoluble material. The supernatant liquid is acidified with 2.5 N hydrochloric acid to pH 1 affording white crystals. The mixture is stirred at room temperature for 20 minutes and filtered. The solids are washed twice with water, once with ethanol and twice with ether and dried affording 854 mg. of a white solid identified by nuclear magnetic resonance as 1 N-ethylcarbamoyl 2-carboxybenzene 4,5-dicarboxylic acid imide.

PREPARATION 3

N-(n-Ethyl)pyromellitic diimide

800 Mg. of 1 N(n-ethyl)carbamoyl 2-carboxybenzene 4,5-dicarboxylic acid imide is suspended in 3 ml. of dry dimethylformamide and immersed in an oil bath at 100° C. whereupon the mixture became homogeneous. The reaction mixture is further heated to 150° C. for 45 minutes. Upon cooling to room temperature, the mixture is stirred overnight and filtered, the solid material is washed once with dimethylformamide, once with alcohol and twice with ether. Upon drying in air, there is afforded white crystals, with a m.p. of 330°–332° C., identified by nuclear magnetic resonance as N-(n-ethyl)pyromellitic diimide.

PREPARATION 4

N-(2-Hydroxyethyl)pyromellitic diimide

300 G. (1.38 mole)pyromellitic imide anhydride is added with stirring at room temperature (23° C.) to a solution of 95% ethanolamine, 83.4 ml. (1.38 mole) in 1.5 l. of dimethylformamide. The mixture is stirred at room temperature for 30 minutes, at 50° C. for 30 minutes, at 75° C. for 30 minutes, at 150° C. for 45 minutes, and then cooled in ice. 3 L. of ethanol was added and cooling is continued until crystallization is complete. The crystals are collected, rinsed with cold ethanol, cold ethyl ether and then dried in vacuo at 70° C. furnishing 292 g. of N-(2-hydroxyethyl)pyromellitic diimide m.p. 274°–5° C. Recrystallization from dimethylformamide gives a purified product m.p. 279°–280° C.

PREPARATION 5

1 N-Methylcarbamoyl-2-carboxybenzene 4,5-dicarboxylic acid anhydride

60 G. of pyromellitic dianhydride is suspended in 800 ml. of acetone and treated with 18.12 g. of 40% aqueous methylamine in 100 ml. of acetone at 10° C. The reaction mixture is stirred for 20 minutes and filtered. The acetone filtrate is evaporated to dryness and the residue triturated with 1000 ml. of refluxing ethylacetate. The mixture is filtered hot, and the insoluble material washed once with hot ethylacetate affording 40.6 g. of 1 N-methylcarbamoyl 2-carboxybenzene 4,5-dicarboxylic acid anhydride m.p. 266°–268° C. Nuclear magnetic resonance confirms the above structure.

PREPARATION 6

N-Methyl benzene 4,5-dicarboxylic acid imide 1,2-1,2-dicarboxylic acid anhydride 39 G. 1 N-methylcarbamoyl 2-carboxybenzene 4,5-dicarboxylic acid anhydride is added to 300 ml. of thionyl chloride and refluxed for 4 hours. The reaction mixture is cooled and diluted with 300 ml. of benzene. The mixture is filtered and the solid material washed once with benzene and 3 times with petroleum ether. The solid is dried at 45° C. in vacuo affording 32.56 g. of N-methyl benzene 4,5-dicarboxylic acid imide 1,2-dicarboxylic acid anhydride m.p. 265°–267° C.

PREPARATION 7

1-Carbamoyl 2-carboxybenzene N-methyl 4,5-dicarboxylic acid amide

15 G. of N-methyl benzene-4,5-dicarboxylic acid imide 1,2-dicarboxylic acid anhydride is suspended in 750 ml. of acetone and treated with ammonia gas at 10° C. for about 10 minutes. The reaction mixture is allowed to warm to room temperature and evaporated to dryness in vacuo. The residue is dissolved in 100 ml. of water and filtered. The water layer is treated with 2.5 N hydrochloric acid to a pH of 1.5 and the resulting precipitate filtered, washed once with water, twice with ethanol, twice with ether and dried at 50° C. in vacuo affording 13.9 g. of 1-carbamoyl 2-carboxybenzene N-methyl 4,5-dicarboxylic acid amide.

PREPARATION 8

N-Methyl pyromellitic diimide 13.9 G. of 1-carbamoyl 2-carboxybenzene N-methyl 4,5-dicarboxylic acid imide is dissolved in 55 ml. of dimethylformamide and heated at reflux for 45 minutes.

The mixture is cooled, diluted with an equal volume of ethanol, filtered, washed once with ethanol and 3 times with ether. The solid material is dried at 100° C. in vacuo affording 8.64 g. of N-methyl pyromellitic diimide m.p. in excess of 320° C.

What is claimed is:

1. A complex having the formula:

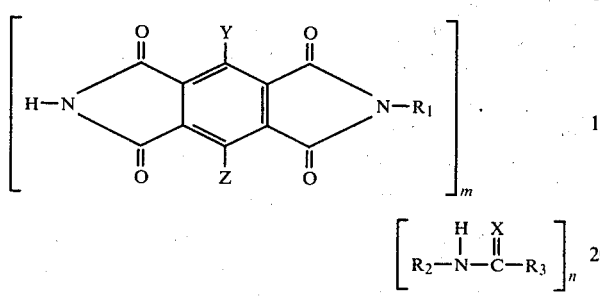

wherein m and n are independently 1 or 2 such that m and n are not both 2;

$R_1$ is hydrogen, loweralkyl, or hydroxy substituted loweralkyl;

Y and Z are independently hydrogen, halogen or loweralkyl;

X is oxygen, sulfur or imino;

$R_2$ and $R_3$ are independently hydrogen, loweralkyl, amino, aminoloweralkyl or loweralkylamino; and $R_2$ and $R_3$ may be connected to form a pyridyl or pyrimidinyl ring which may be optionally substituted with loweralkyl or hydroxy.

2. The complex of claim 1 wherein Y and Z are hydrogen and $R_1$ is hydrogen, methyl, ethyl or hydroxyethyl.

3. The complex of claim 2 wherein Y and Z are hydrogen and $R_1$ is hydrogen, methyl or hydroxyethyl.

4. The complex of claim 1 wherein $R_2$ is hydrogen or loweralkyl; $R_3$ is hydrogen, amino, or lower-alkyl; and X is oxygen.

5. The complex of claim 1 wherein the complexing agent is urea, formamide, acetamide; 2-pyridone or 2- or 4-pyrimidone optionally substituted with methyl, and 2- or 4-hydroxy pyrimidine or amino; optionally substituted with methyl.

6. The complex of claim 5 wherein the complexing agent is selected from urea, formamide, acetamide, 4,6-dimethyl-2-pyrimidone; 2,4-dimethyl-6-pyrimidone; 2-pyridone; 3-hydroxy-2-pyridone and 2-amino-4,6-dimethyl pyrimidine.

7. The complex of claim 6 which is pyromellitic diimide.urea.

8. The complex of claim 6 which is pyromellitic diimide.formamide.

9. The complex of claim 6 which is pyromellitic diimide.acetamide.

10. The complex of claim 6 which is pyromellitic diimide.4,6-dimethyl-2-pyrimidone.

11. A method for increasing the feed efficiency of a ruminant animal which comprises administering to said ruminant in the feed thereof, an effective amount of a compound of claim 1.

* * * * *